US009857870B2

(12) United States Patent
Lee et al.

(10) Patent No.: US 9,857,870 B2
(45) Date of Patent: Jan. 2, 2018

(54) METHOD OF ACQUIRING GAZE INFORMATION IRRESPECTIVE OF WHETHER USER WEARS VISION AID AND MOVES

(71) Applicants: ELECTRONICS AND TELECOMMUNICATIONS RESEARCH INSTITUTE, Daejeon (KR); IUCF-HYU (INDUSTRY-UNIVERSITY COOPERATION FOUNDATION HANYANG UNIVERSITY), Seoul (KR)

(72) Inventors: Hee Kyung Lee, Daejeon (KR); Whoi Yul Kim, Seoul (KR); Hoon Jo, Seoul (KR)

(73) Assignees: ELECTRONICS AND TELECOMMUNICATIONS RESEARCH INSTITUTE, Daejeon (KR); IUCF-HYU(INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 105 days.

(21) Appl. No.: 14/564,550
(22) Filed: Dec. 9, 2014
(65) Prior Publication Data
US 2015/0160725 A1    Jun. 11, 2015
(30) Foreign Application Priority Data

Dec. 10, 2013 (KR) .......................... 10-2013-0153262

(51) Int. Cl.
*G06F 3/01* (2006.01)
*H04N 7/18* (2006.01)
(Continued)

(52) U.S. Cl.
CPC .......... *G06F 3/013* (2013.01); *G06K 9/00604* (2013.01); *G06K 9/209* (2013.01); *H04N 7/144* (2013.01); *H04N 7/18* (2013.01)

(58) Field of Classification Search
CPC .... G06F 3/013; G06K 9/00604; G06K 9/209; H04N 7/144; H04N 7/18
(Continued)

(56) References Cited

U.S. PATENT DOCUMENTS

2012/0133754 A1* 5/2012 Lee .......................... G06F 3/013
                                                                348/78
2013/0285901 A1   10/2013 Lee et al.

FOREIGN PATENT DOCUMENTS

WO    WO 2008141460 A1 * 11/2008   ............. A61B 3/113

OTHER PUBLICATIONS

Takehiko Ohno, and Naoki Mukawa, "A free-head, simple calibration, gaze tracking system that enables gaze based interaction", Eye Tracking Research & Applications, pp. 115-122, 2004.*
(Continued)

*Primary Examiner* — Jamie Atala
*Assistant Examiner* — Ayman Abaza
(74) *Attorney, Agent, or Firm* — Ladas & Parry LLP (57) ABSTRACT

Provided is a gaze tracking apparatus for a user wearing a vision aid, the apparatus including a lighting element unit including a first infrared lighting element and a second infrared lighting element to radiate an infrared light to a user, an image acquirer to acquire an eye image of the user, the eye image including a first corneal reflection light, a second corneal reflection light, a first lens reflection light, and a second lens reflection light, and a processor to turn off the second infrared lighting element when interference occurs between the second lens reflection light and the first corneal reflection light in the acquired eye image, and to compute a gaze position of the user based on user calibration information, and coordinates of the first corneal reflection light.

14 Claims, 9 Drawing Sheets

(51) Int. Cl.
  *H04N 7/14* (2006.01)
  *G06K 9/00* (2006.01)
  *G06K 9/20* (2006.01)
(58) Field of Classification Search
  USPC .......................................................... 348/78
  See application file for complete search history.

(56) References Cited

OTHER PUBLICATIONS

Zhiwei Zhu and Qiang Ji, "Novel Eye Gaze Tracking Techniques Under Natural Head Movement", IEEE Transactions on Biomedical Engineering, vol. 54, No. 12, Dec. 2007.*

Huang Ying, Kong Weiwu and Li Dong, Robust Feature Extraction for Non-contact Gaze Tracking with Eyeglasses, Chinese Journal of Electronics, vol. 22, No. 2, Apr. 2013.*

Craig Hennessey, et al; "Long Range Eye Tracking: Bringing Eye Tracking into the Living Room", Published in: Proceeding ETRA '12 Proceedings of the Symposium on Eye Tracking Research and Applications; pp. 249-252; Mar. 30, 2012.

Zhiwei Zhu, et al; "Novel Eye Gaze Tracking Techniques Under Natural Head Movement", IEEE Transactions on Biomedical Engineering, vol. 54, No. 12, Dec. 2007; pp. 2246-2260.

Dong Hyun Yoo, et al; "A novel non-intrusive eye gaze estimation using cross-ratio under large head motion", Computer Vision and Image Understanding; vol. 98, pp. 25-51, Available online Oct. 12, 2004.

Craig Hennessey: "Eye-Gaze Tracking With Free Head Motion", A Thesis submitted in partial fulfilment of the requirements for the Degree of Master of Applied Science in the Faculty of Graduate Studies (Electrical and Computer Engineering, The University of British Columbia, Aug. 2005, 155 pages.

* cited by examiner

METHOD OF ACQUIRING GAZE INFORMATION IRRESPECTIVE OF WHETHER USER WEARS VISION AID AND MOVES

CROSS-REFERENCE TO RELATED APPLICATION

This application claims the priority benefit of Korean Patent Application No. 10-2013-0153262, filed on Dec. 10, 2013, in the Korean Intellectual Property Office, the disclosure of which is incorporated herein by reference.

BACKGROUND

1. Field of the Invention

Example embodiments of the present invention relate to technology for eliminating a gaze tracking error caused by reflection light generated on a lens of a vision aid due to an infrared lighting element when a user wears the vision aid, in a gaze tracking apparatus for tracking a gaze of the user by using the infrared lighting element.

2. Description of the Related Art

In a gaze tracking method, a position at which a user gazes may be recognized.

The gaze tracking method may provide a similarity to an existing mouse operation protocol, an immediacy of pointing at a gazing area, a convenience of providing a function of an input device to a user having a difficulty in moving a hand, and an immersion provided by adjusting a viewscreen based on a gaze direction of a user.

In lieu of a method of tracking a gaze by devices to be worn on a head of a user, a method of computing a gazing position by installing a camera and a lighting element in an external area rather than being worn by a user may be provided as the gaze tracking method.

In this example, by using an infrared lighting element, an eye image having a reduced amount of image noise may be acquired through the camera and a reflection light, for example, a glint, occurring when an infrared light is reflected from a surface of a cornea may be used to compute gaze information. Since the reflection light is simply and stably detected from an input image by applying image processing technology, the reflection light may be used as a reference point to compute the gaze information for enhancing accuracy and stability of performance in many gaze tracking technologies.

SUMMARY

In a gaze tracking method using a lighting element, when a user wears a vision aid such as glasses and contact lenses, a lens reflection light generated on a lens of the vision aid due to the lighting element may obscure a cornea or a reflection light generated on the cornea.

An aspect of the present invention provides an apparatus for detecting a position of a corneal reflection light and a pupil center from an eye image of a user irrespective of whether the user wears a vision aid.

Another aspect of the present invention also provides an apparatus for tracking an accurate gaze position based on a position of a corneal reflection light and a pupil center detected irrespective of whether a user wears a vision aid.

According to an aspect of the present invention, there is provided a gaze tracking apparatus for a user wearing a vision aid, the apparatus including a lighting element unit including a first infrared lighting element and a second infrared lighting element to radiate an infrared light to the user, an image acquirer to acquire an eye image of the user, the eye image including a first corneal reflection light generated by reflecting, to a pupil of the user, infrared light radiated from the first infrared lighting element, a second corneal reflection light generated by reflecting, to the pupil of the user, infrared light radiated from the second infrared lighting element, a first lens reflection light generated by reflecting, to the vision aid of the user, the infrared light radiated from the first infrared lighting element, and a second lens reflection light generated by reflecting, to the vision aid of the user, the infrared light radiated from the second infrared lighting element, and a processor to eliminate the second lens reflection light when interference occurs between the second lens reflection light and the first corneal reflection light or the second corneal reflection light in the acquired eye image, and to compute a gaze position of the user based on user movement information, user calibration information, and coordinates of the first corneal reflection light.

The user calibration information may include a vector relationship from coordinates of a first calibration corneal reflection light measured at a user calibration position at which the user performs user calibration, to calibration center coordinates between the first calibration corneal reflection light and a second calibration corneal reflection light.

The gaze tracking apparatus may further include a storing unit to, in advance, measure and store coordinates of the first calibration corneal reflection light, coordinates of the second calibration corneal reflection light, and the calibration center coordinates between the first calibration corneal reflection light and the second calibration corneal reflection light when the user is located at the user calibration position.

A gaze tracking may be performed by reflecting, to the user calibration information, movement information of the user moving from the user calibration position to a current position.

According to another aspect of the present invention, there is also provided a method of tracking a gaze of a user wearing a vision aid, the method including radiating infrared light, to the user, from a first infrared lighting element and a second infrared lighting element, respectively, acquiring an eye image of the user, the eye image including a first corneal reflection light generated by reflecting, to a pupil of the user, the infrared light radiated from the first infrared lighting element, a second corneal reflection light generated by reflecting, to the pupil of the user, infrared light radiated from the second infrared lighting element, a first lens reflection light generated by reflecting, to the vision aid of the user, the infrared light radiated from the first infrared lighting element, and a second lens reflection light generated by reflecting, to the vision aid of the user, the infrared light radiated from the second infrared lighting element, eliminating the second lens reflection light when interference occurs between the second lens reflection light and the first corneal reflection light or the second corneal reflection light in the acquired eye image, and computing a gaze position of the user based on user movement information, user calibration information, and coordinates of the first corneal reflection light.

The user calibration information may include a vector relationship from coordinates of a first calibration corneal reflection light measured at a user calibration position at which the user performs user calibration, to calibration center coordinates between the first calibration corneal reflection light and a second calibration corneal reflection light.

The method may further include acquiring and computing position information by performing calibration and actual measurement of a distance separating the infrared lighting element, the narrow-angle camera, an image playback device, the calibration including at least one of stereo calibration, pan-tilt-zoom (PTZ) calibration, and user calibration, acquiring eye position coordinates from an image acquired through a plurality of wide-angle cameras by performing the stereo calibration among the plurality of wide-angle cameras after the actual measurement, extracting information required to control degrees of panning, tilting, and focusing of the narrow-angle camera by performing the PTZ calibration, and computing the position information of the user by performing the user calibration to discern features of each user.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Exemplary embodiments of the present invention have been presented for the purpose of illustration and description. It is not intended to be exhaustive or to limit the invention to the precise form disclosed, and modifications and variations are possible in light of the above teachings or may be acquired from practice of the invention.

The exemplary embodiments of the present invention now will be described more fully hereinafter with reference to the accompanying drawings, in which embodiments of the invention are shown. This invention may, however, be embodied in many different forms and should not be construed as limited to the embodiments set forth herein. Thus, it is intended that the present invention obscures the modifications and variations of this invention provided they come within the scope of the appended claims and their equivalents.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms including technical and scientific terms used herein have the same meaning as commonly understood by one of ordinary skill in the art to which the exemplary embodiments belong. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

Hereinafter, example embodiments will be described in detail with reference to the accompanying drawings.

Figure 1A:
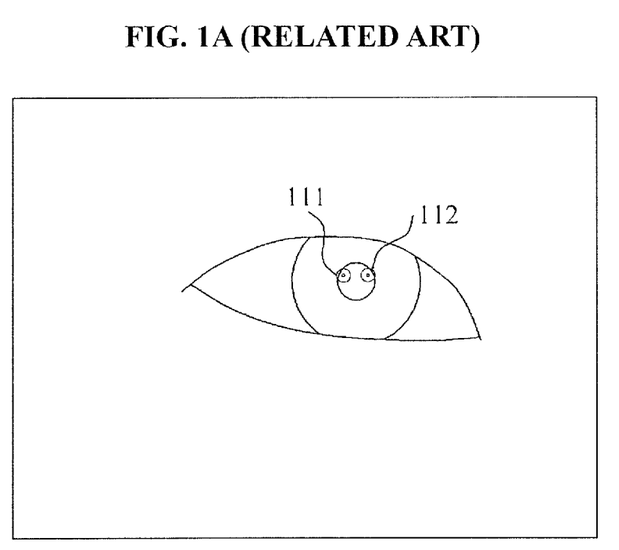
FIGS. 1A and 1B illustrate an issue of lens reflection light that a user wearing a vision aid may experience in an existing gaze tracking method.
Figure 1B:
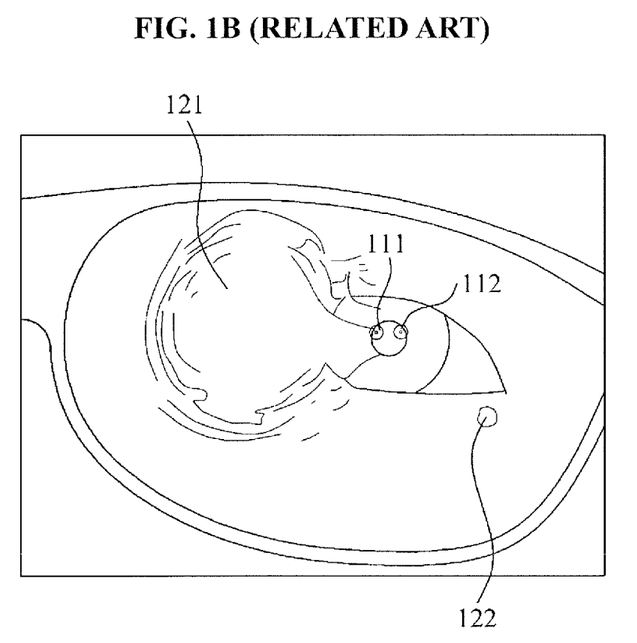

FIGS. 1A and 1B illustrate an issue of lens reflection light that a user wearing a vision aid may experience in an existing gaze tracking method.

Referring to FIGS. 1A and 1B, an effect of lens reflection light may be caused based on whether the vision aid is used. Here, the vision aid may include, for example, glasses and contact lenses.

A difference between a case of wearing the vision aid and a case of not wearing the vision aid may be shown with reference to FIGS. 1A and 1B. In FIG. 1A, when a user does not wear the vision aid, corneal reflection lights 111 and 112 may be generated on a pupil plane of the user. In this case, a gaze tracking apparatus may track a gaze of the user by measuring a center point of the corneal reflection lights 111 and 112. In FIG. 1B, when the user wears the vision aid, a reflection light may be generated on a surface of the vision aid relative to a lens of an infrared lighting element. Thus, when the user wears the vision aid, lens reflection lights 121 and 122 may be generated on a surface of a lens, in addition to the corneal reflection lights 111 and 112 generated in a pupil. An intensity of the reflection light generated on a surface of the vision aid may be greater than an intensity of a corneal reflection light and thus, the reflection light may obscure a pupil area used to compute gaze information. In this case, a pupil center and corneal reflection light may not be detected and thus, the gaze information may not be computed. As described above, when the lens reflection light obscures the pupil center or the corneal reflection light, an error may occur in a process of computing gaze position of the user, or the gaze position may not be detected.

Figure 2:
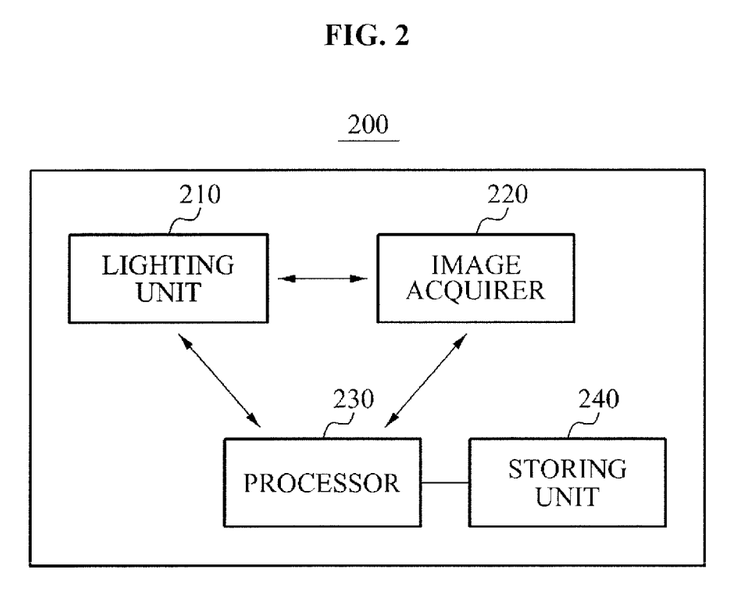
FIG. 2 illustrates an apparatus for tracking a gaze of a user wearing a vision aid according to an example embodiment.

FIG. 2 illustrates an apparatus for tracking a gaze of a user wearing a vision aid according to an example embodiment.

Hereinafter, the apparatus for tracking a gaze may be referred to as a gaze tracking apparatus.

According to an example embodiment, the gaze tracking apparatus may acquire gaze information on the user freely moving over a long distance, irrespective of whether the user wears the vision aid. For example, the gaze tracking apparatus may detect a position of corneal reflection light and a pupil center in an eye image of the user irrespective of whether the user wears the vision aid in an operation range of the gaze tracking apparatus.

The gaze tracking apparatus 200 according to an example embodiment may include a lighting element unit 210, an image acquirer 220, a processor 230, and a storing unit 240.

The lighting element unit 210 may include a plurality of infrared lighting elements to radiate infrared light in a direction of the user. The lighting element unit 210 may include the plurality of infrared lighting elements including a first infrared lighting element and a second infrared lighting element.

The image acquirer 220 may track positions of an eye and a face of the user by acquiring a face image of the user, and acquire an expanded eye image of the user from the tracked eye position. The gaze tracking apparatus 200 may use at least two wide-angle cameras to acquire the face image of the user, and acquire a width of the face, a distance between eyes, and a distance between the eye and a screen based on the acquired face image. In an example, the gaze tracking apparatus 200 may detect positions of the eye and the face from the acquired face image by applying an Adaboost algorithm. The gaze tracking apparatus may acquire the expanded eye image based on the acquired eye position.

The image acquirer 220 may include a narrow-angle camera to acquire the expanded eye image. In this example, the eye image may include a first corneal reflection light, a second corneal reflection light, a first lens reflection light, and a second lens reflection light. The first corneal reflection light may be a reflection light generated by reflecting infrared light radiated from the first infrared lighting element to the pupil of the user. The second corneal reflection light may be a reflection light generated by reflecting infrared light radiated from the second infrared lighting element, to the pupil of the user. The first lens reflection light may be a reflection light generated by reflecting the infrared light radiated from the first infrared lighting element to the vision aid of the user. The second lens reflection light may be a reflection light generated by reflecting the infrared light radiated from the second infrared lighting element to the vision aid of the user.

The image acquirer 220 may include a panning motor (not shown), a tilting motor (not shown), and a focusing motor (not shown), which may rotate a position of the narrow-angle camera such that the narrow-angle camera is directed toward the eye position of the user. The panning motor may control the narrow-angle camera in a leftward or rightward direction. The tilting motor may control the narrow-angle camera in an upward or downward direction. The focusing motor may control the narrow-angle camera to focus on the pupil.

When interference occurs in a process of capturing of two corneal reflection lights in the acquired eye image due to the second lens reflection light, the processor 230 may eliminate the second lens reflection light, and compute a gaze position of the user based on coordinates of the first corneal reflection light and user calibration information. Here, the user calibration information may include a vector relationship from coordinates of a first calibration corneal reflection light measured at a user calibration position corresponding to a position at which the user performs user calibration, to center coordinates between the first calibration corneal reflection light and a second calibration corneal reflection light. In this example, a lens reflection light obscuring a corneal reflection light or the pupil of the user among a plurality of lens reflection lights generated by an infrared lighting element may be used as the second lens reflection light. Thus, a lighting element causing the second lens reflection light may be used as the second infrared lighting element.

As an example, when interference occurs between the second lens reflection light and the first corneal reflection light or the second corneal reflection light in the eye image acquired at a measurement position, the processor 230 may eliminate the second lens reflection light. In this example, the eliminating of the second lens reflection light may indicate obscuring light of the second infrared lighting element or turning-off the second infrared light causing the second lens reflection light. Also, the gaze position of the user may be computed based on the vector relationship from the coordinates of the first calibration corneal reflection light measured when the user is located at the user calibration position, to the center coordinates between the first calibration corneal reflection light and the second calibration corneal reflection light. In this instance, the user calibration position may be a position at which the user performs the user calibration in advance.

The storing unit 240 may measure and store, in advance, coordinates of the first calibration corneal reflection light corresponding to corneal reflection light measured when the user is located at the user calibration position, and coordinates of the second calibration corneal reflection light. In this instance, the storing unit 240 may also store the center coordinates between the first calibration corneal reflection light and the second calibration corneal reflection light. The coordinates of the first calibration corneal reflection light and the coordinates of the second calibration corneal reflection light may be measured and stored in the storing unit 240 in advance.

Movement information to a current position of the user may be computed by acquiring position information of the user through calibration and actual measurement of a distance separating an infrared lighting element, a narrow-angle camera, and an image playback device. Here, the calibration may include at least one of stereo calibration, pan-tilt-zoom (PTZ) calibration, and user calibration. The processor 230 may perform the calibration based on the image acquired by the image acquirer 220. In an embodiment, the stereo calibration between the two wide-angle cameras may be performed to acquire three-dimensional (3D) position coordinates of an object included in a wide-angle camera image. In this example, through the stereo calibration, a degree of rotation and a position of another camera may be estimated based on one wide-angle camera as a reference. In another embodiment, the PTZ calibration may be performed to extract information used for panning, tilting, and focusing the narrow-angle camera from 3D position coordinates. In this example, through the PTZ calibration, the degree of rotation and a degree of focusing of the narrow-angle camera may be determined. In still another embodiment, to discern features of each user, the user calibration may be performed.

User calibration position information may be acquired by performing the calibration and the actual measurement of the distance separating the infrared lighting element, the narrow-angle camera, and the image playback device. Here, the calibration may include at least one of the stereo calibration, the PTZ calibration, and the user calibration.

When the corneal reflection light is obscured by the lens reflection light, the processor 230 may eliminate the second infrared lighting element causing the lens reflection light. In this instance, the gaze position of the user may be computed based on the coordinates of the first corneal reflection light generated by the first infrared lighting element, and the center coordinates between the second calibration corneal reflection light and the first calibration corneal reflection light measured at the stored user calibration position.

For example, by controlling an on/off state of the plurality of infrared lighting elements the processor 230 may locate the second infrared lighting element causing the lens reflection light obscuring the corneal reflection light. In this example, by eliminating the lens reflection light obscuring the corneal reflection light, the gaze position may be computed based on a single corneal reflection light reflected by the first infrared lighting element.

Figure 3:
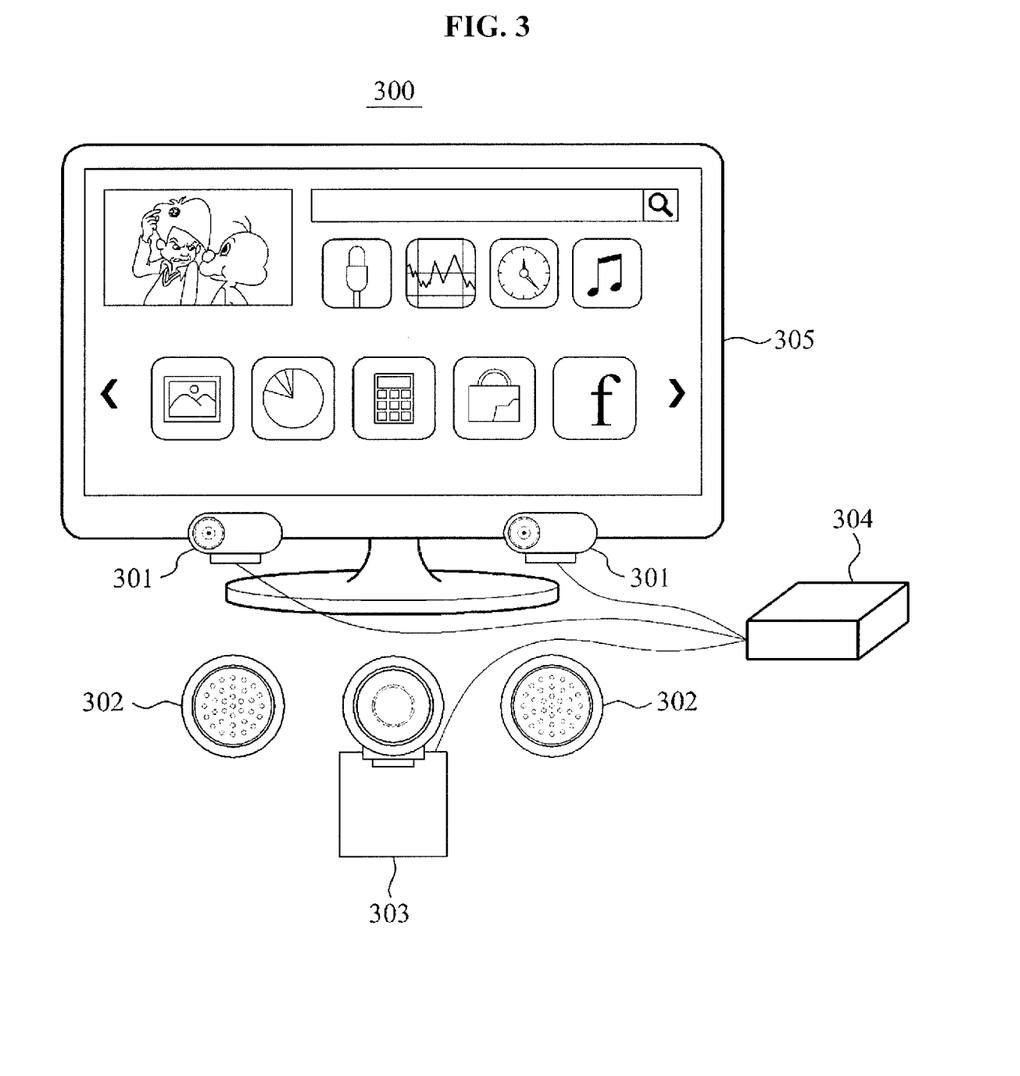
FIG. 3 illustrates a configuration of a gaze tracking apparatus according to an example embodiment.

FIG. 3 illustrates a configuration of a gaze tracking apparatus 300 according to an example embodiment.

The gaze tracking apparatus 300 according to an example embodiment may include a plurality of wide-angle cameras including a wide-angle camera 301, a plurality of infrared lighting elements including an infrared lighting element 302, a narrow-angle camera 303, a processor 304, and an image playback device 305.

According to an example embodiment, an algorithm for eliminating lens reflection light generated on a lens of vision aid may be applied to the gaze tracking apparatus 300.

The narrow-angle camera 303 may include a panning motor (not shown) and a tilting motor (not shown) and a focusing motor (not shown) to control a camera lens.

The plurality of wide-angle cameras may acquire a face image of a user. The wide-angle cameras may recognize an eye position, and control the panning/tilting/focusing motor to control the narrow-angle camera 303 based on the recognized eye position. Also, the narrow-angle camera 303 may acquire an expanded eye image of the user.

The processor 304 may detect center coordinates between two corneal reflection lights generated by two infrared lighting elements from the expanded eye image of the user acquired by the narrow-angle camera 303 and then, compute a gaze position through geometric transformation.

However, as described above, when the user wears the vision aid, a reflection light may be generated on the lens of the vision aid due to the infrared lighting element 302. The reflection light may cause interference in a process of capturing a pupil of the user or acquiring a corneal reflection light generated on the pupil, performed by the narrow-angle camera 303.

The processor 304 may control an on/off state of each of the infrared lighting elements to find an infrared lighting element reflecting lens reflection light causing the interference in the process of capturing the pupil of the user or acquiring corneal reflection light generated on the pupil, performed by the narrow-angle camera 303. In this example, the processor 304 may eliminate a second lens reflection light corresponding to the lens reflection light causing the interference. In this instance, a method of turning off the infrared lighting element causing the second lens reflection light or a method of using a light shield to prevent the infrared lighting element causing the second lens reflection light from facing the user may be used to eliminate the second lens reflection light.

User movement information to a current position may be computed by acquiring position information of the user through calibration and actual measurement of the distance separating the infrared lighting element 302, the narrow-angle camera 303, and the image playback device 305. Here, the calibration may include at least one of stereo calibration, PTZ calibration, and user calibration. In an embodiment, the stereo calibration between the two wide-angle cameras may be performed to acquire 3D position coordinates of an object included in a wide-angle camera image. In this example, through the stereo calibration, a degree of rotation and a position of another camera may be estimated by using a wide-angle camera as a reference. In another embodiment, the PTZ calibration may be performed to extract information used for panning, tilting, and focusing the narrow-angle camera 303 from 3D position coordinates. In still another embodiment, to acknowledge features of each user, the user calibration may be performed.

The gaze tracking apparatus 300 may further include a storing unit to measure and store, in advance, coordinates of a second calibration corneal reflection light and a first calibration corneal reflection light measured when the user is located at a user calibration position, and center coordinates between the first calibration corneal reflection light and the second calibration corneal reflection light.

In an embodiment, the user calibration position may be a reference position at which a rotation angle of a panning motor and a tiling motor controlling the narrow-angle camera 303 is 0 degrees (°). In another embodiment, the user calibration position may be a position at which the user performs user calibration in advance.

The processor 304 may compute the gaze position of the user based on the coordinates of the first corneal reflection light measured when the user is located at a current position from which a gaze is tracked, user movement information from the user calibration position to the current position, and the user calibration information. Here, the user calibration information may correspond to the coordinates of the first calibration corneal reflection light measured when the user is located at the user calibration position, and the center coordinates between the first calibration corneal reflection light and the second calibration corneal reflection light.

Figure 4A:
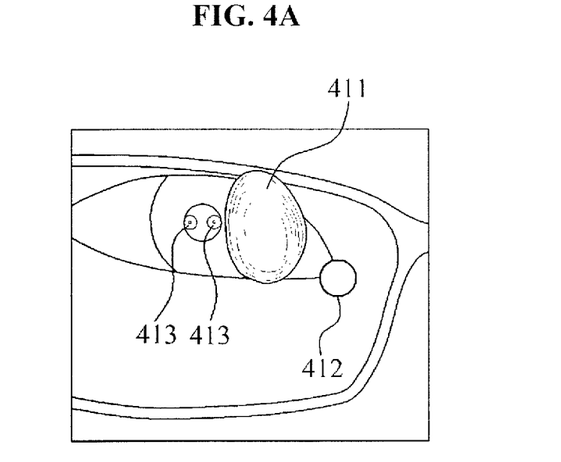
FIGS. 4A and 4B illustrate an example of an effect of eliminating a second infrared light.
Figure 4B:
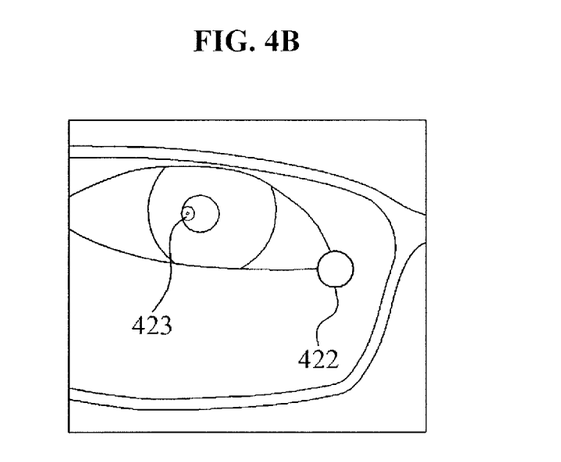

FIGS. 4A and 4B illustrate an example of an effect of eliminating a second infrared light.

Referring to FIGS. 4A and 4B, intensities of the second lens reflection light 411 and a lens reflection light 412 generated on a surface of a vision aid may be greater than intensities of corneal reflection lights 413 generated on a cornea, in general. When infrared light is radiated from two infrared lighting elements to an eye of a user, four reflection lights may be generated from the user wearing the vision aid. Here, the four reflection lights may be a first corneal reflection light, a second corneal reflection light, a first lens reflection light 412, and a second lens reflection light 411. The first corneal reflection light may be a reflection light generated by reflecting infrared light radiated from a first infrared lighting element to a pupil of the user. The second corneal reflection light may be a reflection light generated by reflecting infrared light radiated from a second infrared lighting element to the pupil of the user. The first lens reflection light 412 may be a reflection light generated by reflecting infrared light radiated from the first infrared lighting element to the vision aid of the user. The second lens reflection light 411 may be a reflection light generated by reflecting infrared light radiated from the second infrared lighting element to the vision aid of the user.

When the user is located at a predetermined position, at least one of the second lens reflection light 411 and the first lens reflection light 412 may obscure the pupil and a pupil center or a position of reflection light may not be detected. Thus, an error may occur in a process of computing a gaze position of the user, or the gaze position may not be detected. In FIG. 4A, extracting the corneal reflection lights 413 may be difficult due to the second lens reflection light 411. Here, a lens reflection light obscuring the pupil may correspond to the second lens reflection light 411. In this case, by eliminating an infrared lighting element causing the lens reflection light to obscure the pupil, or a position of a corneal reflection light or the pupil center 423 may be detected.

In FIG. 4B, the second lens reflection light 411 obscuring the pupil may be eliminated. In this example, a first lens reflection light 422 generated due to a first infrared lighting element may not cause interference in a process of capturing the pupil. In an embodiment, when a gaze position is computed, a center point between two corneal reflection lights generated through reflection from two infrared lighting elements to the pupil may be used. However, when one of the two infrared lighting elements is turned off, a position of only a single lens reflection light may be available. In this case, the gaze position of the user may be computed based on the position of the single lens reflection light and calibration coordinates of corneal reflection light measured when the user is located at a user calibration position.

Figure 5A:
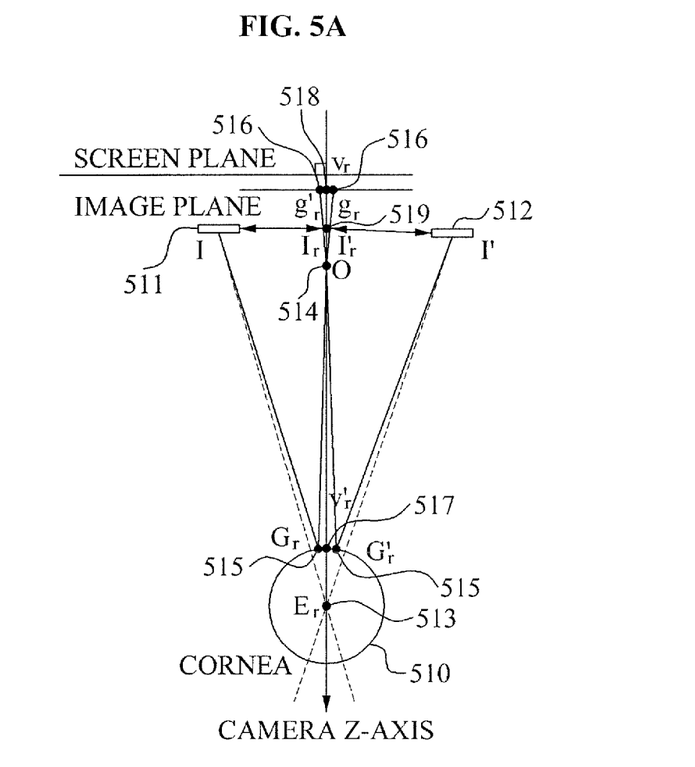
FIGS. 5A through 5C illustrate an apparatus for tracking a gaze through a single corneal reflection light according to an example embodiment.
Figure 5B:
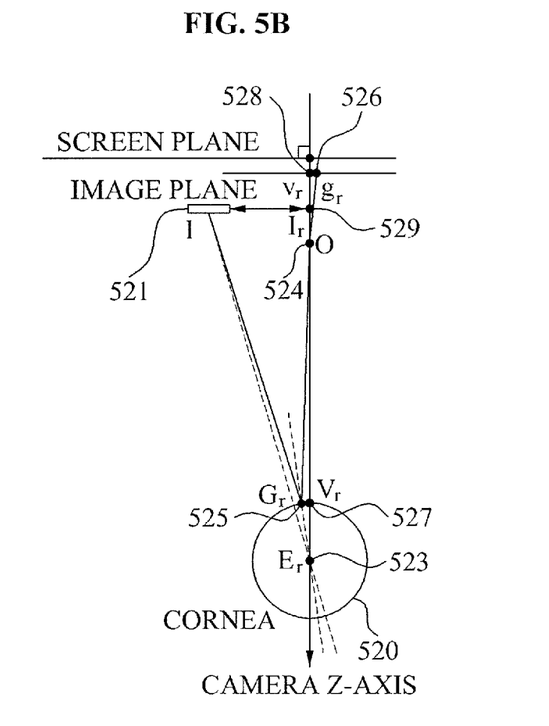
Figure 5C:
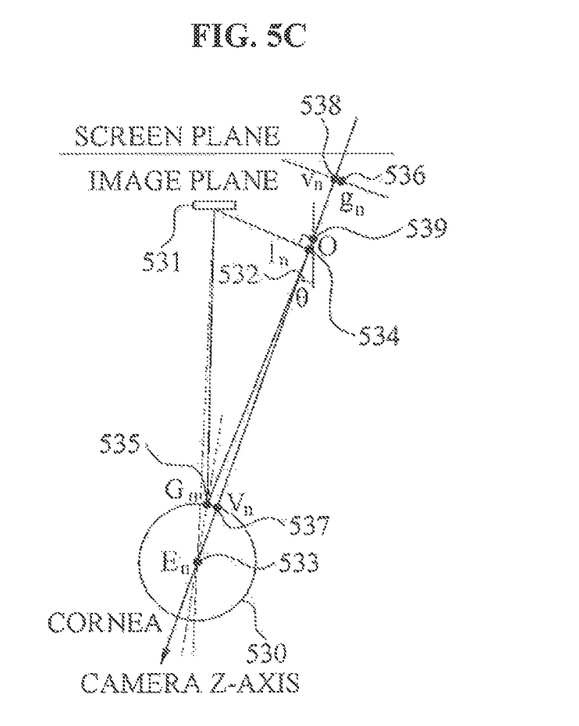

FIGS. 5A through 5C illustrate an apparatus for tracking a gaze through a single conical reflection light according to an example embodiment. Here, a screen plane may be a plane of a monitor screen at which a user gazes, and an image plane may be a plane on which an image is focused, in a narrow-angle camera. A camera Z-axis may be an axis relative to a direction toward which the narrow-angle camera is directed.

A configuration of an apparatus using two infrared lighting elements and an interaction between the apparatus and an eye 510 may be indicated with reference to FIG. 5A. In a case in which a lens reflection light does not obscure a pupil, a processor of the gaze tracking apparatus may detect images 516 and 518 from an eye image acquired through the narrow-angle camera, and may compute a gaze position through geometric transformation. The images 516 and 518 may be acquired when pupil center coordinates 513 and center coordinates 517 of two corneal reflection lights 515 generated by two infrared lighting elements 511 and 512 are focused on the image plane of the narrow-angle camera. Here, an optical center 514 of the narrow-angle camera and an optical axis 519 may be used.

An interaction between the gaze tracking apparatus and an eye 520 when the user is located at a reference position may be indicated with reference to FIG. 5B. When the user is located at the reference position, for example, a position of which a rotation angle of a panning/tilting motor is 0°, a point 525 at which corneal reflection light is generated on a pupil by an infrared lighting element 521, a point 527 assumed to be a center point between two corneal reflection lights, and points 526 and 528 at which the point 525 and the point 527 are focused on an image plane of a narrow-angle camera may be indicated. Here, the point focused on the image plane may be used as reference coordinates stored in a storing unit. Here, an optical center 524 of the narrow-angle camera and an optical axis 529 may be used to compute a gaze position of the user.

An interaction between the gaze tracking apparatus and an eye 530 when a single infrared lighting element is available and the user moves to another position may be indicated with reference to FIG. 5C. When the user is located at a current position, for example, a position of which a rotation angle 532 of the panning/tilting motor is 0 from which a gaze of the user is to be tracked, a point 535 at which corneal reflection light is generated by an infrared lighting element 531 on a cornea of the user located at the current position, a point 537 estimated at a center point between corneal reflection lights generated by two infrared lighting elements, and positions 536 and 538 at which the point 535 and the point 537 are focused on an image plane of a narrow-angle camera may be indicated. Here, an optical center 534 of the narrow-angle camera and an optical axis 539 may be used to compute a gaze position of the user.

In an embodiment, the gaze position of the user may be computed based on coordinates of a first corneal reflection light measured when the user is located at the current position, user movement information, and a reference vector relationship measured when the user is located at the reference position. In this example, the reference vector relationship may use a vector from coordinates of a first reference corneal reflection light, to center coordinates between the first reference corneal reflection light and a second reference corneal reflection light. A processor of the gaze tracking apparatus according to an example embodiment may compute the gaze position of the user using Equation 1.

$$\|\overline{g_n v_n}\| \approx \frac{\|\overline{OE_r}\|\|\overline{\Pi_n}\|\|\overline{IE_r}\|}{\|\overline{OE_n}\|\|\overline{\Pi_r}\|\|\overline{IE_n}\|}\|\overline{g_r v_r}\| \qquad [\text{Equation 1}]$$

In Equation 1, $|\overline{g_n v_n}|$ denotes a distance between predicted center coordinates and coordinates of the first corneal reflection light focused on an image plane of a camera at the current position, $|\overline{OE_r}|$ denotes a distance between a center point of an eye of the user located at the reference position and an optical center of the narrow-angle camera, $|\overline{\Pi_n}|$ denotes a distance from an infrared lighting element to an optical axis 519 of the narrow-angle camera facing the eye of the user located at the current position, and $|\overline{IE_r}|$ denotes distance from the infrared lighting element to the center point of the eye of the user located at the reference position. $|\overline{OE_n}|$ denotes a distance from the optical center of the narrow-angle camera to the center point of the eye of the user located at the current position, $|\overline{\Pi_r}|$ denotes a distance from the infrared lighting element to the optical axis of the narrow-angle camera facing the eye of the user located at the reference position, $|\overline{IE_n}|$ denotes a distance from the infrared lighting element to the center point of the eye of the user located at the current position, and $|\overline{g_r v_r}|$ denotes a distance from the coordinates of the first reference corneal reflection light, which is focused on the image plane of the camera, of the user located at the reference position, to the center coordinates between the first reference corneal reflection light and the second reference corneal reflection light.

Equation 1 according to an example embodiment may be obtained using Equations 2 and 3.

$$\frac{r\sin\left(\arcsin\left(\frac{\|\overline{\Pi_r}\|}{\|\overline{IE_r}\|}\right)/2\right)}{\|\overline{OE_r}\|} = \frac{\|\overline{g_r v_r}\|}{f} \qquad [\text{Equation 2}]$$

$$\frac{r\sin\left(\arcsin\left(\frac{\|\overline{\Pi_n}\|}{\|\overline{IE_n}\|}\right)/2\right)}{\|\overline{OE_n}\|} = \frac{\|\overline{g_n v_n}\|}{f}$$

-continued $$\|\vec{g_n v_n}\| = \frac{\|\overrightarrow{OE_r}\|\sin\left(\arcsin\left(\frac{\|\vec{II_n}\|}{\|\vec{IE_n}\|}\right)/2\right)}{\|\overrightarrow{OE_n}\|\sin\left(\arcsin\left(\frac{\|\vec{II_r}\|}{\|\vec{IE_r}\|}\right)/2\right)}\|\vec{g_r v_r}\| \quad \text{[Equation 3]}$$

In Equation 2 and Equation 3, subscripts r and n denote the reference position and the current position, respectively. $\|\vec{II_r}\|$ denoting a distance from an infrared lighting element 521 to an optical axis 529 of the narrow-angle camera may be actually measured in a configuration of the apparatus. $\|\overrightarrow{OE_r}\|$ and $\|\overrightarrow{OE_n}\|$ denoting distances from an optical center 524 of the narrow-angle camera to center points 523 and 533 of the eye of the user may be computed by dividing a projection matrix P into an intrinsic matrix K, a rotation matrix R, a translation matrix t, regarding the center points 523 and 533 of the eye of the user as $E_r=(x_r, y_r, z_r)$ and $E_n=(x_n, y_n, z_n)$ and regarding positions of the infrared lighting elements 521 and 531 as $I=(x_i, y_i, z_i)$ when a projection matrix corresponding to a result obtained through pan/tilt calibration is P=K[R|t] as shown in Equation 4.

$$|\overrightarrow{OE_r}|=|R(x_r, y_r, z_r)^T+t|$$

$$|\overrightarrow{OE_n}|=|R(x_n, y_n, z_n)^T+t|.$$

Subsequently, when $\|\vec{II_n}\|$ may be obtained by computing $I_n=(I_{nx}, I_{ny}, I_{nz}))$ in Equation 5 using a matrix $R_p$ in which a panning angle $\theta_p$ is reflected, and a matrix $R_t$ in which a tilting angle $\theta_t$ is reflected from the reference position of the narrow-angle camera when the narrow-angle camera is rotated by $\theta_p$ and $\theta_t$ by a pan/tilt module, and by computing a distance between actual infrared lighting elements.

$$(I_{nx}, I_{ny}, I_{nz})^T = R_t R_p (I_{rx}, I_{ry}, I_{rz})^T \quad \text{[Equation 5]}$$

$$R_t = \begin{bmatrix} 1 & 0 & 0 \\ 0 & \cos\theta_t & -\sin\theta_t \\ 0 & \sin\theta_t & \cos\theta_t \end{bmatrix},$$

$$R_p = \begin{bmatrix} \cos\theta_p & 0 & \sin\theta_p \\ 0 & 1 & 0 \\ -\sin\theta_p & 0 & \cos\theta_p \end{bmatrix}$$

Distances $\|IE_r\|$, $\|IE_n\|$ between the measured center points $E_r$, $E_n$ and the lighting element position I which is discerned in advance may be obtained using Equation 6. Here, vectors to a lighting element and the narrow-angle camera may be assumed to be $\vec{II_r}=(D_{xr}, D_{yr})$, $\vec{II_n}=(D_{xn}, D_{yn})$.

$$|\vec{IE_r}|=\sqrt{D_{xr}^2+D_{yr}^2+(|\overrightarrow{OE_r}|+|\overrightarrow{OI_r}|)^2}$$

$$|\vec{IE_n}|=\sqrt{D_{xn}^2+D_{yn}^2+(|\overrightarrow{OE_n}|+|\overrightarrow{OI_n}|)^2}$$

To compute the gaze position, the gaze tracking apparatus according to an example embodiment may use information associated with a process by which user calibration is previously performed by the user. Equation 1 indicating a relationship between the reference position and the current position may be reestablished based on a relationship between the current position and a user calibration position of the user. When the user calibration position is expressed as a subscript c, Equation 7 may be as follows.

$$\|\vec{g_n v_n}\| \approx \frac{\|\overrightarrow{OE_c}\|\|\vec{II_n}\|\|\vec{IE_c}\|}{\|\overrightarrow{OE_n}\|\|\vec{II_c}\|\|\vec{IE_n}\|}\|\vec{g_c v_c}\| \quad \text{[Equation 7]}$$

In Equation 7, $|\vec{g_n v_n}|$ denotes a distance between predicted center coordinates and coordinates of the first corneal reflection light focused on an image plane of a camera at the current position, $|\overrightarrow{OE_c}|$ denotes a distance between a center point of an eye of the user located at the user calibration position and an optical center of the narrow-angle camera, $|\vec{II_n}|$ denotes a distance from an infrared lighting element to an optical axis of the narrow-angle camera facing the eye of the user located at the current position, and $|\vec{IE_c}|$ denotes distance from the infrared lighting element to the center point of the eye of the user located at the user calibration position. $|\overrightarrow{OE_n}|$ denotes a distance from the optical center of the narrow-angle camera to the center point of the eye of the user located at the current position, $|\vec{II_c}|$ denotes a distance from the infrared lighting element to the optical axis of the narrow-angle camera facing the eye of the user located at the user calibration position, $|\vec{IE_n}|$ denotes a distance from the infrared lighting element to the center point of the eye of the user located at the current position, and $|\vec{g_c v_c}|$ denotes a distance from the coordinates of the first calibration corneal reflection light, which is focused on the image plane of the camera, of the user located at the user calibration position, to the center coordinates between the first calibration corneal reflection light and the second calibration corneal reflection light.

When the reference position is changed to be the user calibration position, reference information may correspond to user calibration information. Here, the user calibration information may include a vector relationship from the coordinates of the first calibration corneal reflection light measured at the user calibration position at which the user performs the user calibration, to calibration center coordinates between the first calibration corneal reflection light and the second calibration corneal reflection light.

A calibration position according to an example embodiment may be a position at which the first calibration corneal reflection light and the second calibration corneal reflection light may be comprehensively acquired without interference caused by lens reflection light.

Accordingly, the gaze position of the user may be computed by reflecting movement information, for example, $$\frac{\|\overrightarrow{OE_c}\|\|\vec{II_n}\|\|\vec{IE_c}\|}{\|\overrightarrow{OE_n}\|\|\vec{II_c}\|\|\vec{IE_n}\|}$$

to the vector relationship, for example, $|\vec{g_c v_c}|$ from the coordinates of the first calibration corneal reflection light measured when the user is located at the user calibration position, to the center coordinates between the first calibration corneal reflection light and the second calibration corneal reflection light.

Figure 6:
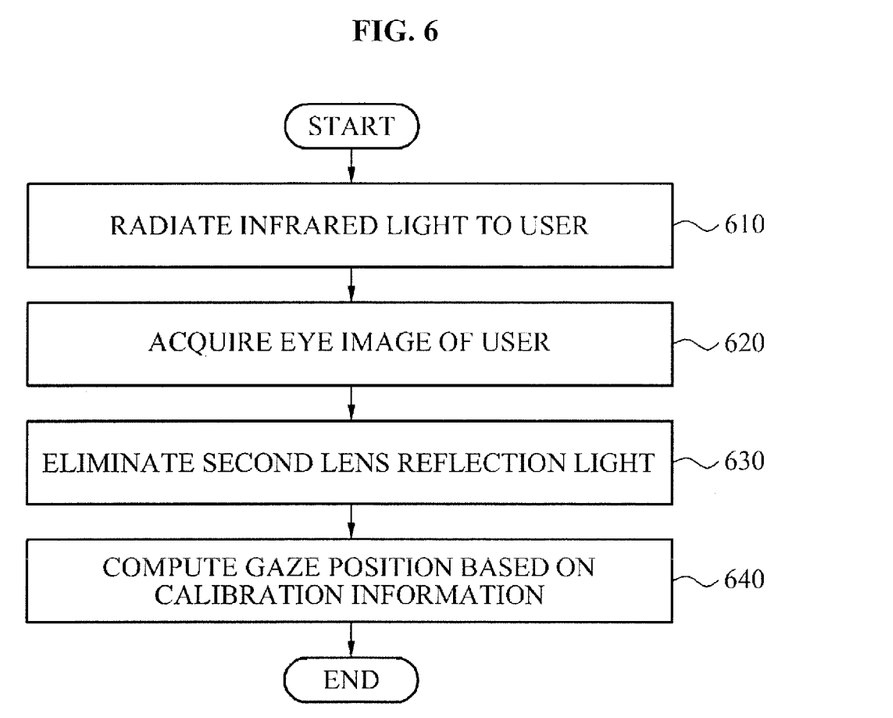
FIG. 6 illustrates a method of tracking a gaze of a user wearing a vision aid according to an example embodiment.

FIG. 6 illustrates a gaze tracking method of tracking a gaze of a user wearing a vision aid according to an example embodiment.

The method of tracking a gaze of a user wearing a vision aid may be provided with reference to FIG. 6.

In operation 610, infrared lights may be radiated from a first infrared lighting element and a second infrared lighting element, respectively.

In operation 620, an eye image of the user may be acquired using the radiated infrared lights.

According to an example embodiment, in operation 620, position information of the user may also be computed by performing calibration among a plurality of wide-angle cameras, a narrow-angle camera, and an image playback device. In an embodiment, a face image of the user may be acquired using the plurality of wide-angle cameras. In the gaze tracking method according to an example embodiment, positions of an eye and a face may be detected from the acquired face image by applying an Adaboost algorithm. An expanded eye image may be acquired using the narrow-angle camera by panning and tilting the narrow-angle camera based on the detected position of the eye. In the gaze tracking method according to an example embodiment, the expanded eye image may be acquired based on the acquired position of the eye.

In this instance, the expanded eye image may include a first corneal reflection light, a second corneal reflection light, a first lens reflection light, and a second lens reflection light. The first corneal reflection light may be a reflection light generated by reflecting infrared light radiated from the first infrared lighting element to the pupil of the user. The second corneal reflection light may be a reflection light generated by reflecting infrared light radiated from the second infrared lighting element to the pupil of the user. The first lens reflection light may be a reflection light generated by reflecting the infrared light radiated from the first infrared lighting element to the vision aid of the user. The second lens reflection light may be a reflection light generated by reflecting the infrared light radiated from the second infrared lighting element to the vision aid of the user.

In operation 620, the positions of the eye and the face may be detected by applying an Adaboost algorithm to the face image acquired by the wide-angle camera. In an embodiment, an eye image may be acquired by panning/tilting/focusing controlling a position of the narrow-angle camera such that the narrow-angle camera faces the position of the eye of the user using a motor based on information on an eye position.

In operation 630, when interference occurs between the second lens reflection light and the first corneal reflection light or the second corneal reflection light in the acquired eye image, the second lens reflection light may be eliminated. In this instance, the second lens reflection light may be eliminated by turning off a second infrared lighting element and eliminating an infrared lighting element generating lens reflection light obscuring a corneal reflection light.

According to an example embodiment, the lens reflection light obscuring the corneal reflection light or the pupil of the user among a plurality of lens reflection lights generated by infrared lighting elements may correspond to the second lens reflection light. Thus, a lighting element generating the second lens reflection light may correspond to the second infrared lighting element. In an example, when interference occurs between the second lens reflection light and corneal reflection lights in the acquired eye image, the second infrared lighting element generating the second lens reflection light may be eliminated.

In operation 640, a gaze position of the user may be computed based on user calibration information measured when the user is located at a user calibration position, and coordinates of the first corneal reflection light. Here, the user calibration information may include a vector relationship from coordinates of a first calibration corneal reflection light measured at a calibration position at which the user performs a user calibration, to calibration center coordinates between the first calibration corneal reflection light and a second calibration corneal reflection light.

Accordingly, the coordinates of the first calibration corneal reflection light and the second calibration corneal reflection light generated by the first infrared lighting element and the second infrared lighting element when the user is located at the user calibration position may be measured and stored in advance. The user calibration information may correspond to the coordinates of the first calibration corneal reflection light and the coordinates of the second calibration corneal reflection light, which are measured in advance when the user is located at the user calibration position.

In an example, in an operation of acquiring the eye image of the user, eye position coordinates may be acquired from an image acquired through stereo calibration performed by the plurality of wide-angle cameras. In another example, in the operation of acquiring the eye image of the user, information necessary for controlling degrees of panning, tilting, and focusing of the narrow-angle camera by performing PTZ calibration may also be extracted.

The units described herein may be implemented using hardware components and software components. For example, the hardware components may include microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums.

The methods according to the above-described embodiments may be recorded, stored, or fixed in one or more non-transitory computer-readable media that includes program instructions to be implemented by a computer to cause a processor to execute or perform the program instructions. The media may also include, alone or in combination with the program instructions, data files, data structures, and the like. The program instructions recorded on the media may be those specially designed and constructed, or they may be of the kind well-known and available to those having skill in the computer software arts. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations and methods described above, or vice versa.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A gaze tracking apparatus comprising:
a lighting element unit comprising a first infrared lighting element and a second infrared lighting element to radiate an infrared light to a user;
an image acquirer to acquire an eye image of the user, the eye image comprising a first corneal reflection light generated by reflecting, to a pupil of the user, infrared light radiated from the first infrared lighting element, a second corneal reflection light generated by reflecting, to the pupil of the user, infrared light radiated from the second infrared lighting element, a first lens reflection light generated by reflecting, to a vision aid of the user, the infrared light radiated from the first infrared lighting element, and a second lens reflection light generated by reflecting, to the vision aid of the user, the infrared light radiated from the second infrared lighting element; and
a processor to eliminate the second lens reflection light when interference occurs between the second lens reflection light and the first corneal reflection light or the second corneal reflection light in the acquired eye image, and to compute a gaze position of the user based on user movement information, user calibration information, and coordinates of the first corneal reflection light,
wherein the second lens reflection light is a lens reflection light obscuring a corneal reflection light or the pupil of the user among a plurality of lens reflection lights generated by an infrared lighting element;
the second infrared lighting element is a lighting element causing the second lens reflection light; and
the processor controls an on/off state of the lighting element unit to search for the second infrared lighting element that causes the second lens reflection light, removes the second infrared lighting element, and computes the gaze position of the user based on the first reflected cornea light reflected by the first infrared lighting element.

2. The apparatus of claim 1, wherein the user calibration information comprises a vector relationship from coordinates of a first calibration corneal reflection light measured at a user calibration position at which the user performs user calibration, to calibration center coordinates between the first calibration corneal reflection light and a second calibration corneal reflection light.

3. The apparatus of claim 2, further comprising:
a storing unit to, in advance, measure and store coordinates of the first calibration corneal reflection light, coordinates of the second calibration corneal reflection light, and the calibration center coordinates between the first calibration corneal reflection light and the second calibration corneal reflection light when the user is located at the user calibration position.

4. The apparatus of claim 2, wherein the image acquirer comprises a plurality of wide-angle cameras, and
wherein the processor acquires eye position coordinates from an image acquired through the wide-angle cameras by performing stereo calibration among the plurality of wide-angle cameras.

5. The apparatus of claim 4, wherein the image acquirer further comprises a narrow-angle camera and a panning motor, a tilting motor, and a focusing motor to control the narrow-angle camera, and
wherein the processor performs pan-tilt-zoom (PTZ) calibration, and extracts information required to control the panning motor, the tilting motor, and the focusing motor such that the narrow-angle camera is directed toward the acquired eye image.

6. The apparatus of claim 5, wherein the processor computes position information of the user by performing calibration among the plurality of wide-angle cameras, the narrow-angle camera, an image playback device, and the user.

7. The apparatus of claim 5, wherein the processor computes a gaze position of the user using an equation $$\|\overline{g_n v_n}\| \approx \frac{\|\overline{OE_c}\|\|\overline{II_n}\|\|\overline{IE_c}\|}{\|\overline{OE_n}\|\|\overline{II_c}\|\|\overline{IE_n}\|}\|\overline{g_c v_c}\|,$$

and
wherein $|\overline{g_n v_n}|$ denotes a distance between predicted center coordinates and coordinates of the first corneal reflection light focused on an image plane of a camera at a current position, $|\overline{IE_c}|$ denotes a distance between an optical center of the narrow-angle camera and a center point of an eye of the user located at the user calibration position, $|\overline{II_n}|$ denotes a distance from an infrared light to an optical axis of the narrow-angle camera facing the eye of the user located at a current position, $|\overline{IE_c}|$ denotes a distance from the infrared light to the center point of the eye of the user located at the user calibration position, $|\overline{OE_n}|$ denotes a distance between the optical center of the narrow-angle camera and the center point of the eye of the user located at the current position, $|\overline{II_c}|$ denotes a distance from the infrared light to the optical axis of the narrow-angle camera facing the eye of the user located at the user calibration position, $|\overline{IE_n}|$ denotes a distance from the infrared light to the center point of the eye of the user located at the current position, and $|\overline{g_c v_c}|$ denotes a distance from center coordinates between the first calibration corneal reflection light and the second calibration corneal reflection light, to the coordinates of the first calibration corneal reflection light of the user located at the user calibration position focused on an image plane of the narrow-angle camera.

8. A gaze tracking method comprising:
radiating infrared light, to a user, from a first infrared lighting element and a second infrared lighting element, respectively;
acquiring an eye image of the user, the eye image comprising a first corneal reflection light generated by reflecting, to a pupil of the user, the infrared light radiated from the first infrared lighting element, a second corneal reflection light generated by reflecting, to the pupil of the user, infrared light radiated from the second infrared lighting element, a first lens reflection light generated by reflecting, to a vision aid of the user, the infrared light radiated from the first infrared lighting element, and a second lens reflection light generated by reflecting, to the vision aid of the user, the infrared light radiated from the second infrared lighting element;
eliminating the second lens reflection light when interference occurs between the second lens reflection light and the first corneal reflection light or the second corneal reflection light in the acquired eye image; and
computing a gaze position of the user based on user movement information, user calibration information, and coordinates of the first corneal reflection light,
wherein the second lens reflection light is a lens reflection light obscuring a corneal reflection light or the pupil of the user among a plurality of lens reflection lights generated by an infrared lighting element;
the second infrared lighting element is a lighting element causing the second lens reflection light; and
the computing comprises controlling an on/off state of the lighting element unit to search for the second infrared lighting element that causes the second lens reflection light, removing the second infrared lighting element, and computing the gaze position of the user based on the first reflected cornea light reflected by the first infrared lighting element.

9. The method of claim 8, wherein the user calibration information comprises a vector relationship from coordinates of a first calibration corneal reflection light measured at a user calibration position at which the user performs user calibration, to calibration center coordinates between the first calibration corneal reflection light and a second calibration corneal reflection light.

10. The method of claim 9, further comprising:
measuring and storing, in advance, coordinates of the first calibration corneal reflection light, coordinates of the second calibration corneal reflection light, and the calibration center coordinates between the first calibration corneal reflection light and the second calibration corneal reflection light when the user is located at the user calibration position.

11. The method of claim 9, wherein the gaze tracking method further comprises:
acquiring eye position coordinates from an image acquired through a plurality of wide-angle cameras by performing stereo calibration among the plurality of wide-angle cameras;
performing pan-tilt-zoom (PTZ) calibration, and extracting information required to control degrees of panning, tilting, and focusing of a narrow-angle camera; and
computing position information of the user by performing calibration among the plurality of wide-angle cameras, the narrow-angle camera, an image playback device, and the user.

12. The method of claim 9, wherein the computing comprises acquiring user movement information from a user calibration position to a current position and computing the vector relationship by reflecting the acquired user movement information.

13. The method of claim 12, wherein the acquiring of the movement information comprises:
computing user calibration position information by performing calibration among a plurality of wide-angle cameras, a narrow-angle camera, an image playback device, and the user at the user calibration position;
computing current position information of the user by performing the calibration among the plurality of wide-angle cameras, the narrow-angle camera, the image playback device, and the user at the current position; and
acquiring the user movement information based on the user calibration position information and the current position information.

14. A method of eliminating a gaze tracking error caused by non-retroreflective light generated on a lens of a vision aid worm by a user, comprising:
radiating infrared light, to the user, from a first infrared lighting element and a second infrared lighting element, respectively;
acquiring a single non-retroreflective eye image of the user, the eye image comprising a first corneal reflection light generated by reflecting, to a pupil of the user, the infrared light radiated from the first infrared lighting element, a second corneal reflection light generated by reflecting, to the pupil of the user, infrared light radiated from the second infrared lighting element, a first lens reflection light generated by reflecting, to a vision aid of the user, the infrared light radiated from the first infrared lighting element, and a second lens reflection light generated by reflecting, in non-retroreflective fashion, to the vision aid of the user, the infrared light radiated from the second infrared lighting element;
determining when an interference occurs between the second lens reflection light and the first corneal reflection light or the second corneal reflection light in the acquired eye image;
eliminating the interference caused by the second lens reflection light by using a light shield to prevent the second infrared light element from causing the second lens reflection light; and
computing a gaze position of the user based on user movement information, user calibration information, and coordinates of the first corneal reflection light.

* * * * *